United States Patent
Krakovits et al.

(10) Patent No.: US 6,344,059 B1
(45) Date of Patent: *Feb. 5, 2002

(54) KNEE SURFACE REPLACEMENT PROSTHESIS

(76) Inventors: Gabor Krakovits, u. 81, H-1026 Budapest Torokvesz (HU); Zoltan Juharosi, u. 44, H-1238 Budapest Erzebet (HU); Tamasne Bardosi, u. 80, H-1204 Budapest Eperjes (HU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,664
(22) PCT Filed: Feb. 14, 1997
(86) PCT No.: PCT/HU97/00006
§ 371 Date: Dec. 3, 1998
§ 102(e) Date: Dec. 3, 1998
(87) PCT Pub. No.: WO97/30663
PCT Pub. Date: Aug. 28, 1997

(30) Foreign Application Priority Data

Feb. 26, 1996 (HU) ............................................... 9600445

(51) Int. Cl.$^7$ ................................................. A61F 2/38
(52) U.S. Cl. .................................. 623/20.31; 623/20.14
(58) Field of Search ...................... 623/20, 20.11–20.36

(56) References Cited

U.S. PATENT DOCUMENTS

| | | | |
|---|---|---|---|
| 4,659,331 A | 4/1987 | Mathews et al. | 623/20 |
| 4,714,473 A | 12/1987 | Bloebaum | 623/20 |
| 4,731,086 A | 3/1988 | Whiteside et al. | 623/20 |
| 5,133,758 A | 7/1992 | Hollister | 623/20 |
| 5,203,807 A | 4/1993 | Evans et al. | 623/20 |
| 5,358,527 A | * 10/1994 | Forte | 623/20 |
| 5,609,639 A | * 3/1997 | Walker | 623/20 |
| 5,683,468 A | * 11/1997 | Pappas | 623/20 |
| 5,702,458 A | * 12/1997 | Burstein et al. | 623/20 |
| 5,800,552 A | * 9/1998 | Forte | 623/20 |
| 5,871,546 A | * 2/1999 | Colleran et al. | 623/20 |

FOREIGN PATENT DOCUMENTS

| | | | |
|---|---|---|---|
| EP | 0 522822 A1 | * | 1/1993 |
| GB | 2150441 | | 7/1985 |
| GB | 2219942 | | 12/1989 |
| WO | 0328463 | | 1/1989 |
| WO | 90522822 | | 7/1992 |

* cited by examiner

Primary Examiner—Corrine McDermott
Assistant Examiner—Hieu Phan
(74) Attorney, Agent, or Firm—Ladas & Parry

(57) ABSTRACT

The invention relates to a replacement knee prosthesis having a femoral component (1) provided with lock pins for attachment to femoral condyls and a plastic tibial component (2) placed in a metal tray (3) fixed to the tibia by means of a pin or a screw. The replacement knee prosthesis is characterized in that the lateral surface of its femoral component (1) has a movement determined by their conical surfaces which is formed in accordance with its logarithmic spiral generatrix (4) while its medial surface corresponds to the conical spiral generatrix (5).

6 Claims, 6 Drawing Sheets

KNEE SURFACE REPLACEMENT PROSTHESIS

TECHNICAL FIELD

The present invention relates to the surface configuration of knee replacement prosthesis comprising a femoral component provided with lock pins for attachment to femoral conalyls and a plastic tibial component placed in a metal tray fixed to the tibia by means of a pin or a screw.

BACKGROUND ART

The injured knee joint can be replaced by an artificial knee joint. In cases where high degrees of shape deformations are to be corrected, the necessary movements can only be ensured by a tight mechanical connection of the two surfaces. Various hinged and axial total prostheses are used for such purposes. The disadvantage of the well known prostheses is that after the removal of the bone fragments the large quantity of metal is covered by only a thin layer of human tissue i.e. only by the human skin. Another disadvantage is that the bearing providing the connection can not be positioned physiologically, which may lead to the prosthesis becoming loose.

If the ligament systems providing the function of a rope system and limiting the sliding of the two surfaces on each other are intact, it is sufficient to replace only the surface participating in the movement. In these cases, so-called surface replacement prostheses are used.

In the case of these so-called surface replacement prostheses only a smaller part of the bone end must be removed. They have no mechanical connection.

PRIOR ART

The femoral component of the known surface replacement prostheses consists of two slides positioned on the condyle opposite to which a plastic block combined with a metal tray is placed on the tibia.

The femoral component consists essentially of two approximately parallel rolls as described by Fick at the beginning of the century when this has become known in the technical literature as the so-called Fick principle. The shape of these rolls is approximately ellipsoidal and the center of the generatrix curves is located on a spiral so-called evolute. This ensures a tight connection of the two bones in accordance with the components of the knee joint during flexion and extension of the knee.

The femoral component of most of the known knee prostheses is a mirrored symmetrical duplicate of prostheses corresponding to a prosthesis designed to one condyle, which, however, does not correspond to the normal threedimensional movement of the knee.

A considerable part of the known knee prostheses has a flat plane opponent element which results in a sliding of the components on each other, which damages the stability of the knee-joint. Meanwhile there is a single point connection between the curved femoral component and the plane surface causing an excessive abrasion on a plastic tibial component.

In known solutions where the oppsion element is a plastic part in the shape of a trough, but due to its geometry does not allow the end rotation, therefore a rotation stress develops between the prosthesis and the bone, which may lead to a dislocation of the prosthesis component. To overcome this, rotation a rotatable plastic insert is positioned in a metal tray like rotable base. In this case the prosthesis may inhibit rotation because of the connective tissue of the human body, which causes pain. The stops limiting the movement and transmitting the forces, which may cause dislocation at the bone boundary in their end position.

Dislocations can be eliminated e.g. by application of anchoring procedures disclosed in the CH 665 55; UK 2 150 441; UK 2 219 942; U.S. Pat No. 4,659,331; U.S. Pat. No. 4,714,473 and U.S. Pat. No. 4,731,086 Patent Specifications.

In most known prostheses the depth of the trough in the sagittal plane of the opposite element is essentially constant. Such a solution is disclosed in the DE 2 550774 Patent Specification. The disadvantage of this embodiment is that the knee may be sprained backwards when the leg is extended.

The common disadvantage of the known knee prostheses discussed above is that the movements necessary during the normal human life can not be ensured without any difficulty. Meanwhile the movements or the abrasion of the components may cause a wear taking place very quickly or a mechanical loosening of the prosthesis.

SUMMARY OF THE INVENTION

The purpose of the present invention is the establishment of a prosthesis for replacing the surface of the human knee joint comprising components for realizing the normal movements necessary for perfect function of the knee-joint by sliding and rolling on each other.

During the creation of the knee prosthesis according to the invention it was started from the assumption that joints in humans and animals have evolved according to the needs of their movement and that their final shape ensures perfect functioning.

Accordingly, the essence of this invention is to form the shape of the surfaces of the prosthesis participating in the movements, which differs significantly from those of currently known knee surface replacement prostheses.

The invention is based on the recognition—which has already been supported by three-dimensional analysis—that "spherical movement of a rigid body" known from mechanics is realized by means of the new prosthesis.

The purpose of the invention is achieved by a knee surface replacement prosthesis consisting of a femoral component provided with lock pins and a plastic tibial component placed in a metal tray fixed to the tibia by means of a pin or a screw wherein the lateral or external surface of its femoral component having a movement determined by conical surfaces, is formed by the logarithmic spiral generatrix playing a role in the movement while its medial or internal surface corresponds to the conical spiral generatrix.

In a preferred embodiment of the knee surface replacement prosthesis according to the invention the circular arcs—circle segments—running along the generatrix of the femoral component are shaped perpendicularly to the logarithmic spiral generatrix in the case of the lateral surface while in the case of the medial surface they are formed rotatable along the conical spiral generatrix in accordance with the segment curves of the human knee-joint.

In another preferred embodiment of the knee surface replacement prosthesis according to the invention, the surface of the tibial component is provided with a trough-shaped notch, whose surface of the exterior arch of this trough-shaped notch is formed in accordance with the rolling down the logarithmic spiral generatrix of the femoral component while of its medial surface corresponds to the rolling down of the conical spiral generatrix of the femoral component.

In a further preferred embodiment of the knee surface replacement prosthesis according to the invention the trough-shaped camber of the tibial component is higher than that of the femoral component.

BRIEF DESCRIPTION OF THE DRAWINGS

The knee surface replacement prosthesis according to the invention will now be described by way of example with reference to the appended drawings, wherein.

DETAILED DESCRIPTION OF THE DRAWINGS

Figure 1:
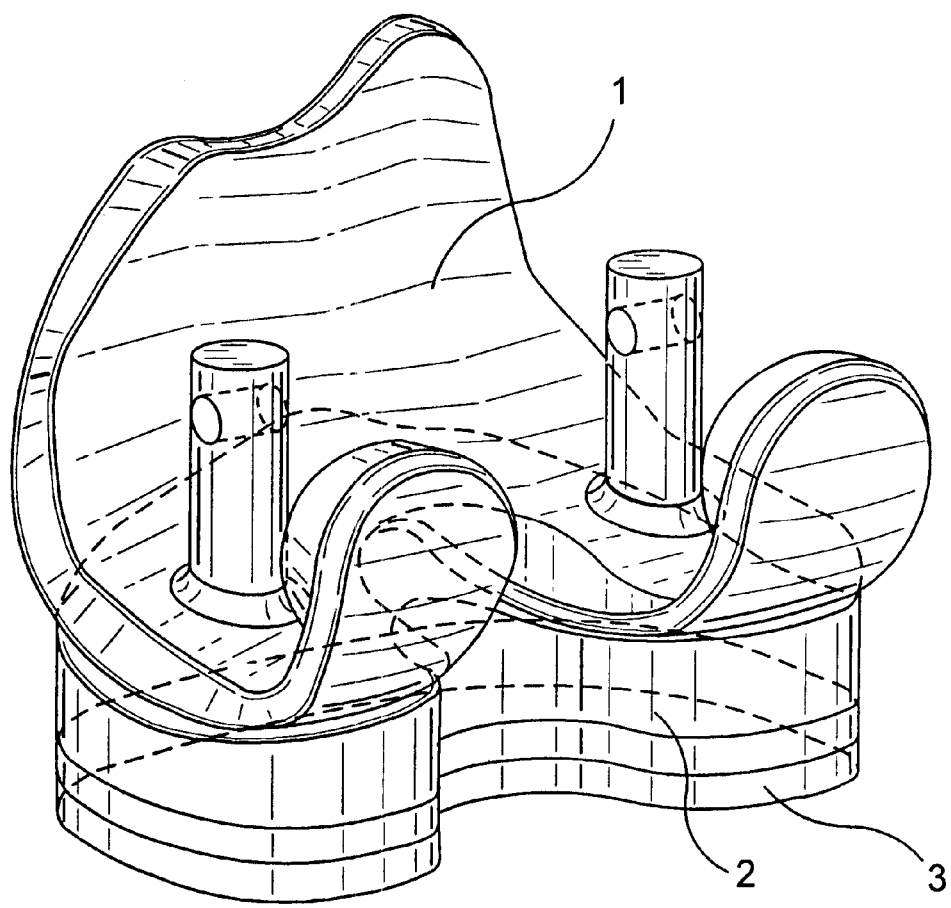
FIG. 1. shows an axonometric view of the knee surface replacement prosthesis according to the invention.

The knee surface replacement prosthesis shown in FIG. 1 consists essentially of a femoral component 1 and a tibial component 2 as well as a metal tray 3 for fixing the tibial component 2 which itself is already known.

FIG. 1 shows a double-sided embodiment.

Figure 2:
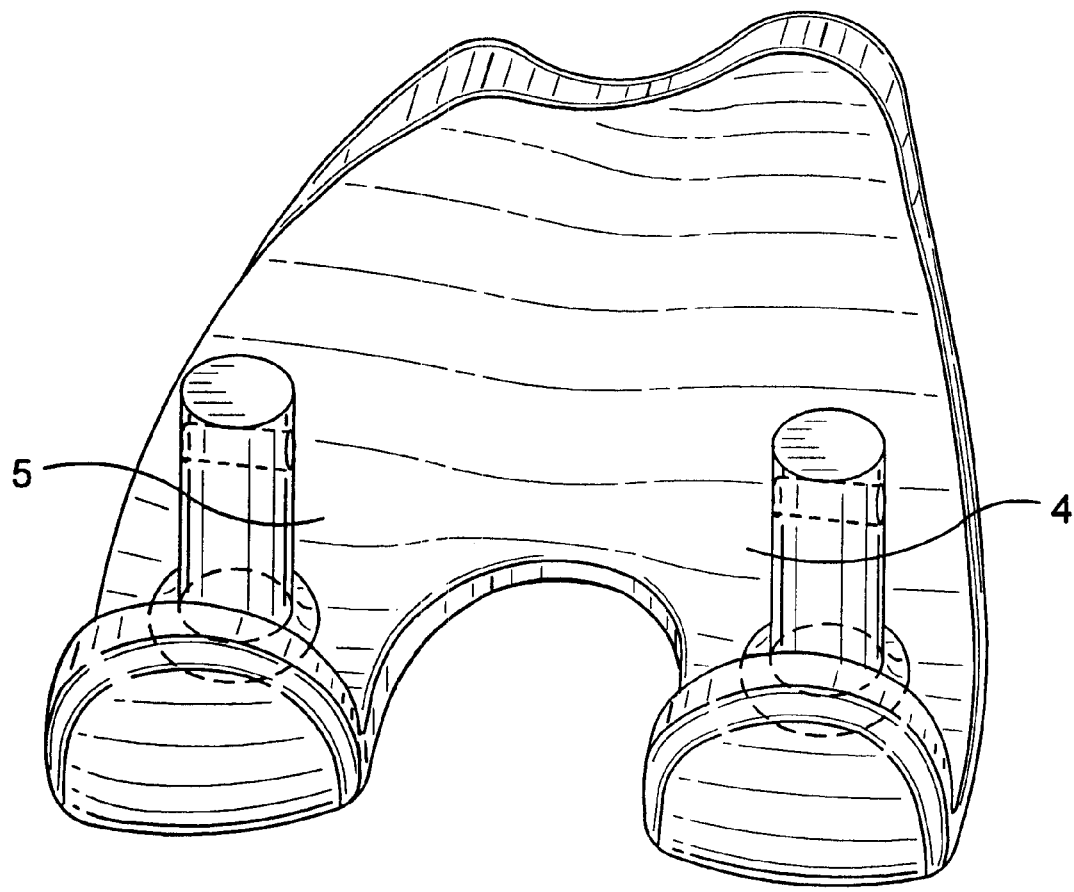
FIG. 2. shows an axonometric view of the femoral component of the knee surface replacement prosthesis according to FIG. 1. illustrating the generatrix of the external and internal surface.

FIG. 2 is an axonometric drawing of the femoral component 1 shown in FIG. 1 illustrating the lateral or external surface of the logarithmic spiral generatrix 4 and the medial or internal surface of the conical spiral generatrix 5 which play a role in the movement.

Figure 3:
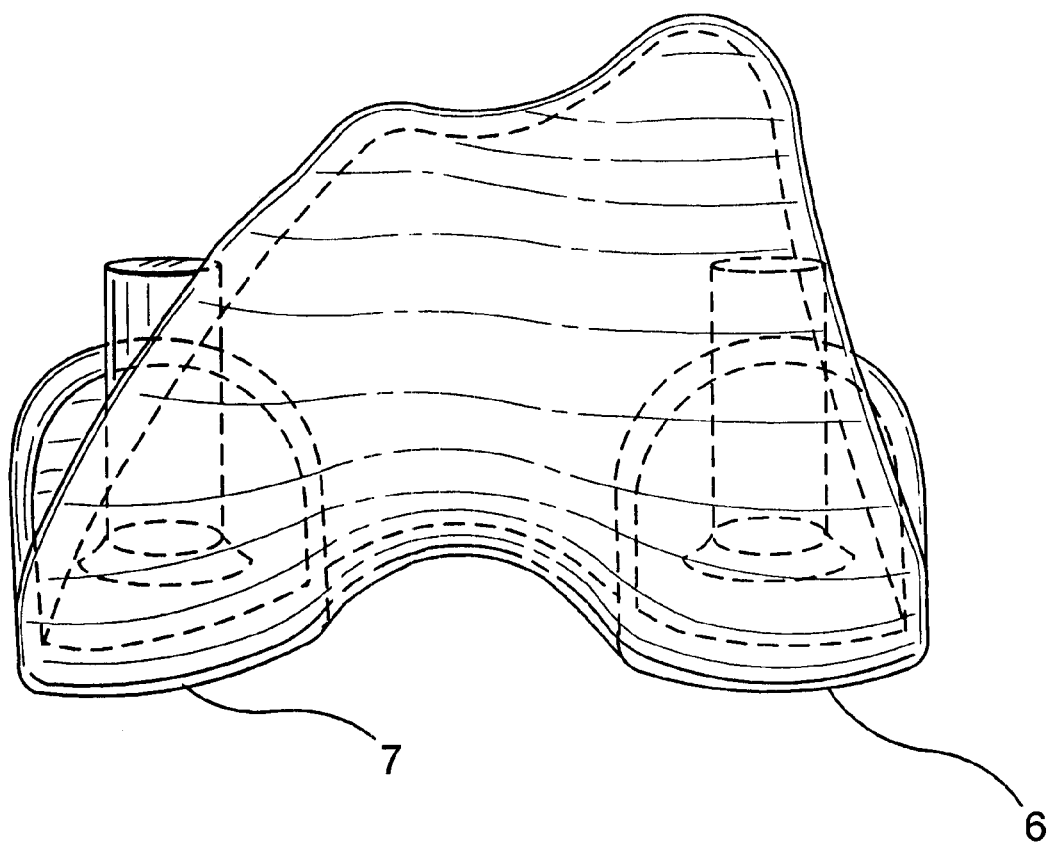
FIG. 3. shows a rear view of the femoral component according to FIG. 2, illustrating the circle segments.

FIG. 3 is a rear view of the femoral component shown in FIG. 1 illustrating the circle segment 6 perpendicular to the logarithmic spiral generatrix 4 and the circle segments 7 rotated spatially in an appropriate degree along the conical spiral generatrix 5 of the femoral component.

Figure 4:
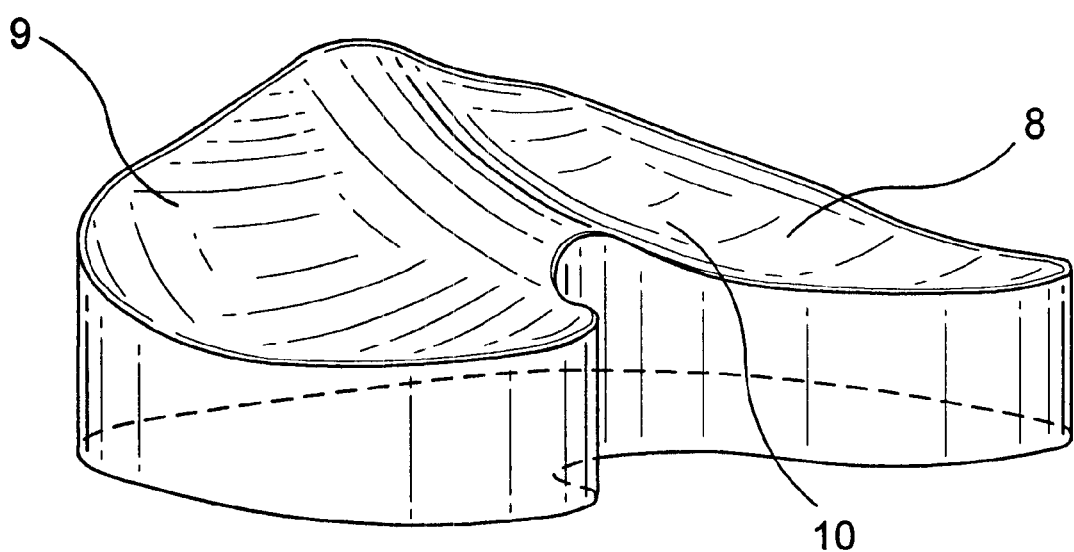
FIG. 4. shows an axonometric drawing of tibial component of the knee surface replacement prosthesis according to FIG. 1.

FIG. 4 is an axonometric drawing of the trough-shaped surfaces 8 and 9 implemented in accordance with the rolling down of the logarithmic spiral generatrix 4 and the conical spiral generatrix 5 of the femoral component 1. It has also a significant sagittal plane camber, the protrusion of the frontal part prevents the knee from spraining backwards. The camber 10 of the tibial component 2 in frontal plane is higher than that of the femoral component 1, so that the freedom of movement is allowed and simultaneously all external mechanical influences acting on a body are compensated.

For realizing the spherical movement of a rigid body the surfaces of the femoral component 1 playing a role the movement are shaped as a so-called polhodic cone. The generatrix of the lateral or external surface is the logarithmic spiral generatrix 4 while that of the medial or internal surface is conical spiral generatrix 5.

The counterpart, i.e. the tibial component 2 which is positioned in the conventional metal tray 3 is formed so that it is trough-shaped.

The surface 8 of the trough-shaped lateral or external arc of the tibial component 2 is formed in accordance with the rolling down of the logarithmic spiral generatrix 4 of the femoral component 1 while the surface 9 of its medial or internal arc corresponds to the rolling down of the conical spiral generatrix 5 of the femoral component 1.

The equation of the logarithmic spiral generatrix 4 of the femoral component 4 is as follows:

$$p = c e^{k\Phi}$$

$$(\pi/6 \leq \Phi \leq 2\pi/3)$$

where "c" is a constant characteristic of the curvatures of the condyle; in accordance with the population; "k" is the cotangent, characteristic of the population and also testing to avoid self-locking, of the tangent of the condyle section in the sagittal plane.

The equation of the conical spiral generatrix 5 of the femoral component 1 is as follows:

$$x = a e^{k\Phi} \cos \Phi$$

$$y = a e^{k\Phi} \sin \Phi$$

$$k = b e^{k\Phi}$$

where "a" and "b" are constants depending on the femur width and the largest condyle "radius" measured in the frontal plane, characteristic of the population.

The thus formed femoral component 1 and tibial component 2 constitute a prosthesis pair, between the components of which the movement along the arc on the cone results in rotation, i.e. a joint movement that corresponds to the physiological movement (spherical movement) even during crouching.

The medial surface of the femoral component 1 is surrounded by five planes. This matches the bone surfaces created during and operation by a pattern generally known.

The tibial component 2 is a plastic block, the trough-shaped camber 10 of which is higher than that of the circle segments 6, 7 of the femoral component 1 to provide a certain degree of freedom of movement and to flexibly counteract nonphysiological forces.

The two-parameter equation of the lateral surface of the femoral component 1 is as follows:

$$x = ([c e^{k\Phi} - R] + R \cos \theta) \cos \Phi$$

$$y = ([c e^{k\Phi} - R] + R \cos \theta) \sin \Phi$$

$$z = \pm R \sin \theta$$

where θ is the central angle of the circle arc segment with R=35 mm.

The two-parameter equation of the medial surface of the femoral component 1 is as follows:

$$x = ([a e^{k\Phi} - R] + R \cos \theta) \cos \Phi$$

$$y = ([a e^{k\Phi} - R] + R \cos \theta) \sin \Phi$$

$$z = a e^{k\Phi} \pm R \sin \theta$$

where θ is the central angle of the circle arc segment with R=35 mm.

Besides the double-sided prostheses it is also necessary to use single-sided prostheses. Such single-sided prostheses form half of a double sided knee-prostheses having lateral and medial curves. Thus their function-allows the respective physiological movements.

Figure 5:
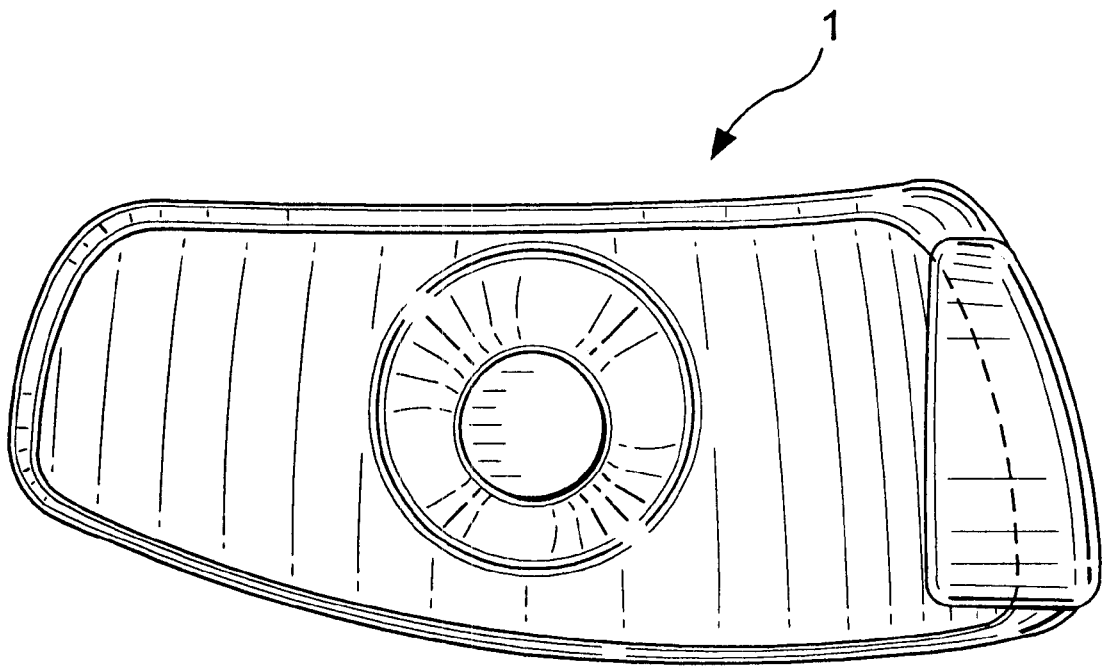
FIG. 5. shows a top view of another, single-sided embodiment applied on the internal condyle of the femur according to FIG. 2.

FIG. 5 shows such a single-sided femoral component 1, the generatrix of which is provided with a curve which corresponds to the conical spiral generatrix 5 of the medial surface of the femoral component 1.

Figure 6:
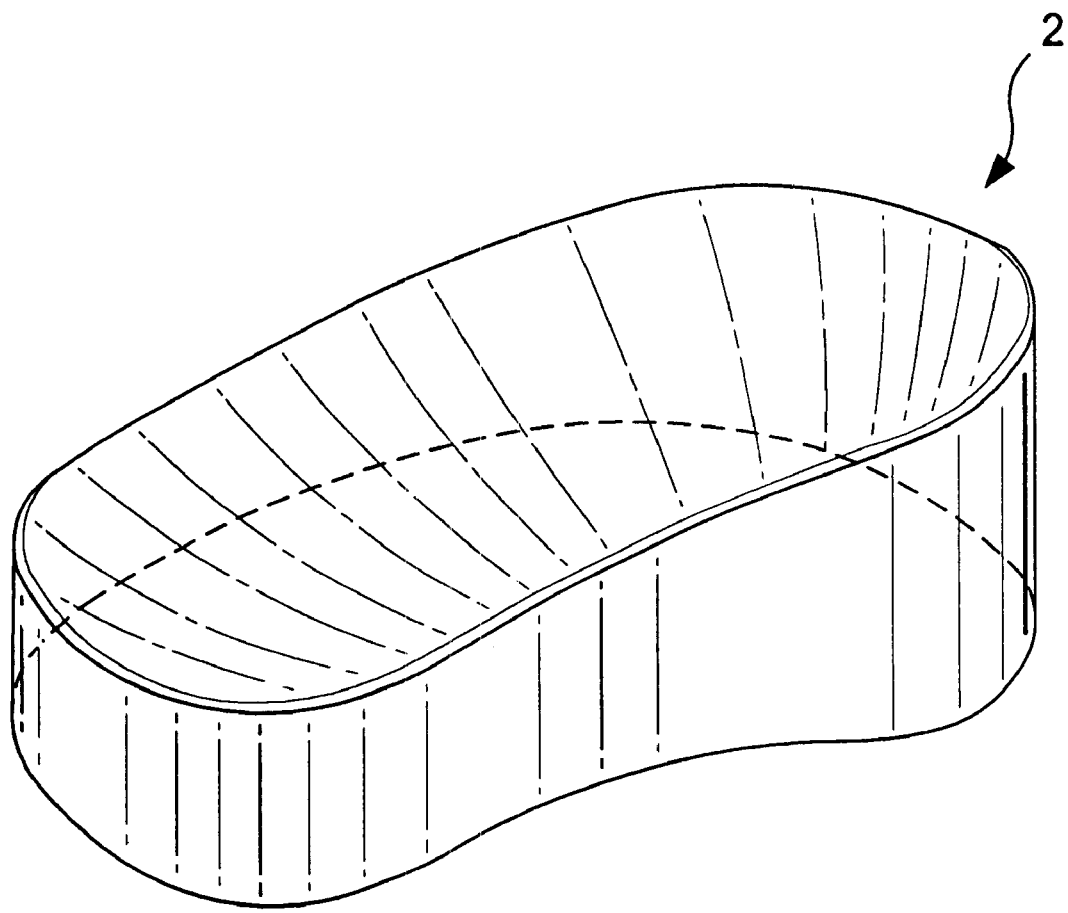
FIG. 6. shows an axonometric drawing of another single-sided embodiment of the knee surface replacement prosthesis according to FIG. 4 applied on the internal tibial plateau.

FIG. 6 shows the tibial component 2 of a single-sided knee surface replacement prosthesis, the rolling down of the trough-like shaped surface of which corresponds to the rolling down of the femoral component 1 according to FIG. 5.

The single-sided femoral component 1—FIG. 5—has a so-called anatomical internal surface. It has the advantage that only a minimal part of the bone surface should be removed, while the condyle retains its anatomical shape and hence its bone structure.

The shell-like seating provides a stability that makes anchoring procedures mentioned in the prior art superfluous even in the case of any cementless application.

The advantage of the knee surface replacement prosthesis according to the invention is that it provides the physiologically normal movements which are possible because of the anatomical structure of the bones forming the knee joint, which is ensured by the logarithmic spiral generatrix of the lateral surface of the femoral component 1, the conical spiral generatrix of its medial surface as well as the trough-shaped cambers of the tibial component 2 which corresponds to their movement.

What is claim is:

1. A replacement knee prosthesis comprising a femoral component (1) for attachment to the femur of a user and a plastic tibial component placed in a metal tray (3) which can be fixed to the tibia of the user, the femoral component (1) having a lateral surface generated by a logarithmic spiral generatrix (4) and a medial surface generated by a conical spiral generatrix (5), said tibial component (2) having a camber (10) of trough-like shape in which a lateral surface (8) of the trough-like shape camber corresponds to a rolling-down of said logarithmic spiral generatrix (4) of the femoral component (1) and a medial surface (9) of the trough-like shape camber corresponds to the rolling-down of said conical spiral genatric (5) of the femoral component (1), wherein said lateral surface of the femoral component is defined by a two parameter equation as follows:

$$x=([ce^{k\Phi}-R]+R\cos\theta)\cos\Phi$$

$$y=([ce^{k\Phi}-R]+R\cos\theta)\sin\Phi$$

$$z=\pm R\sin\theta$$

where $\theta$ is the central angle of the circle arc segment with R=35 mm said medial surface of the femoral component being defined by the two parameter equation as follows:

$$x=([ae^{k\Phi}-R]+R\cos\theta)\cos\Phi$$

$$y=([ae^{k\Phi}-R]+R\cos\theta)\sin\Phi$$

$$z=ae^{k\Phi}\pm R\sin\theta$$

where $\theta$ is the central angle of the circle arc segment with R=35 mm.

2. A replacement knee prosthesis according to claim 1, wherein circle segments (6) on the lateral surface of the femoral component (1) are perpendicular to the logarithmic spiral generatrix (4), and circle segments (7) on the medial surface of the femoral component (1) are rotatable along the conical spiral generatrix (5) for corresponding to segment curves of the knee joint of the user.

3. A replacement knee prosthesis according to claim 1, wherein the trough-like shape camber (10) of the tibial component (2) has a height greater than that of the circle segments (6, 7) of the femoral component (1).

4. A knee surface replacement prosthesis comprising a femoral component (1) and a plastic tibial component (2) placed in a metal tray (3) to be fixed to the tibia, the femoral component (1) having a lateral condyle with a lateral surface generated by a logarithmic spiral generatrix (4), the tibial component (2) having a camber (10) of trough-like shape, said femoral component having a medial condyle with an internal medial surface with a different curvature from that of said lateral surface and generated by a conical spiral generatrix (5), the trough-like shape tibial component having a lateral notch (2) corresponding to a form obtained by rolling-down said logarithmic spiral generatrix (4) of the femoral component (1), the trough-like shaped tibial component also having an internal medial notch (2) corresponding to a form obtained by rolling-down said conical spiral generatrix (5) of the femoral component (1).

5. The knee surface replacement prosthesis according to claim 4, wherein perpendicular to the logarithmic spiral generatrix (4) the lateral surface of the femoral component (1) is formed by circle segments (6), and perpendicular to the conical spiral generatrix (5) the internal medial surface of the femoral component (1) is formed by circle segments (76).

6. The knee surface replacement prosthesis according to claim 4, wherein the trough-like shaped camber (1) of the tibial component (2) is greater in said notches than that of the femoral component (1).

* * * * *